(12) United States Patent
Brusco et al.

(10) Patent No.: US 8,030,946 B2
(45) Date of Patent: Oct. 4, 2011

(54) IN-PIPE COATING INTEGRITY MONITOR FOR VERY LONG PIPES

(75) Inventors: Matias Brusco, Katy, TX (US); Anour Jamoussi, Sugar Land, TX (US); Roderic K. Stanley, Houston, TX (US); Fathi H. Ghorbel, Pearland, TX (US)

(73) Assignee: itRobotics, Inc., Stafford, TX (US)

( * ) Notice: Subject to any disclaimer, the term of this patent is extended or adjusted under 35 U.S.C. 154(b) by 0 days.

(21) Appl. No.: 12/835,510

(22) Filed: Jul. 13, 2010

(65) Prior Publication Data
US 2010/0277188 A1    Nov. 4, 2010

Related U.S. Application Data

(63) Continuation-in-part of application No. 11/844,845, filed on Aug. 24, 2007, now Pat. No. 7,768,270.

(60) Provisional application No. 60/839,884, filed on Aug. 24, 2006.

(51) Int. Cl.
*G01N 27/00* (2006.01)
*G01N 27/28* (2006.01)

(52) U.S. Cl. .......... 324/557; 324/559; 324/238

(58) Field of Classification Search ........... 324/557
See application file for complete search history.

(56) References Cited

U.S. PATENT DOCUMENTS

| | | | |
|---|---|---|---|
| 2,979,656 A | 8/1957 | Stearns | |
| 3,614,605 A | 10/1971 | Eisele | |
| 5,828,219 A * | 10/1998 | Hanlon et al. | 324/529 |
| 6,067,846 A | 5/2000 | Hill | |
| 6,474,165 B1 * | 11/2002 | Harper et al. | 73/623 |
| 6,917,176 B2 | 7/2005 | Schempf | |
| 7,768,270 B2 * | 8/2010 | Brusco et al. | 324/557 |
| 2001/0052778 A1 * | 12/2001 | Smith | 324/541 |
| 2004/0217759 A1 | 11/2004 | Burkhardt | |
| 2005/0217394 A1 | 10/2005 | Langley | |
| 2007/0182425 A1 | 8/2007 | Byerley | |
| 2008/0048682 A1 | 2/2008 | Brusco | |

FOREIGN PATENT DOCUMENTS
WO    WO2007130723 A1    11/2007

OTHER PUBLICATIONS
PCT Search Report for related application PCT/US07/61575.
* cited by examiner

*Primary Examiner* — Jeff Natalini
(74) *Attorney, Agent, or Firm* — Bracewell & Giuliani, LLP

(57) ABSTRACT

Systems, methods and program products of instructions stored on a computer readable medium related to a tether free piggable inspection tool capable of detecting holidays and able to read and store non-conductive internal coating thickness values in very long conductive pipes, along with distance values for further off-line analysis, are provided. The inspection tool includes a plurality of thickness probes, a data storage unit, a control unit, a plurality of navigation wheels and a holiday detector that uses an electrical conductive medium, such as a gas or fluid, as the ground connection. A closed loop configuration is adopted allowing the system to autocorrect itself for different coating thicknesses along the pipe.

20 Claims, 3 Drawing Sheets

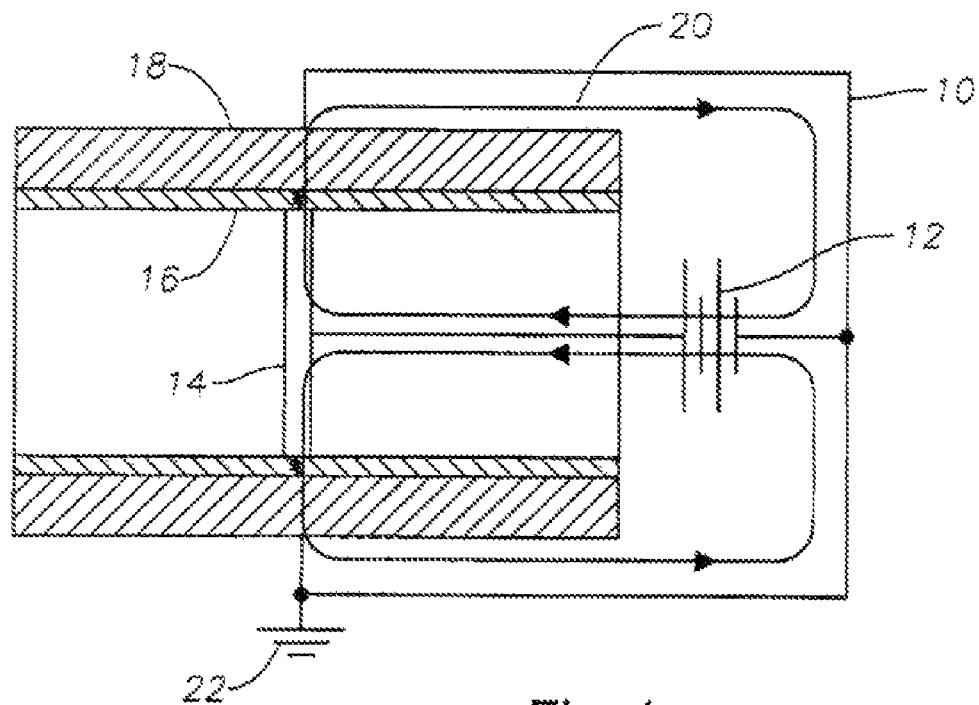
Fig. 1
(Prior Art)
Fig. 3
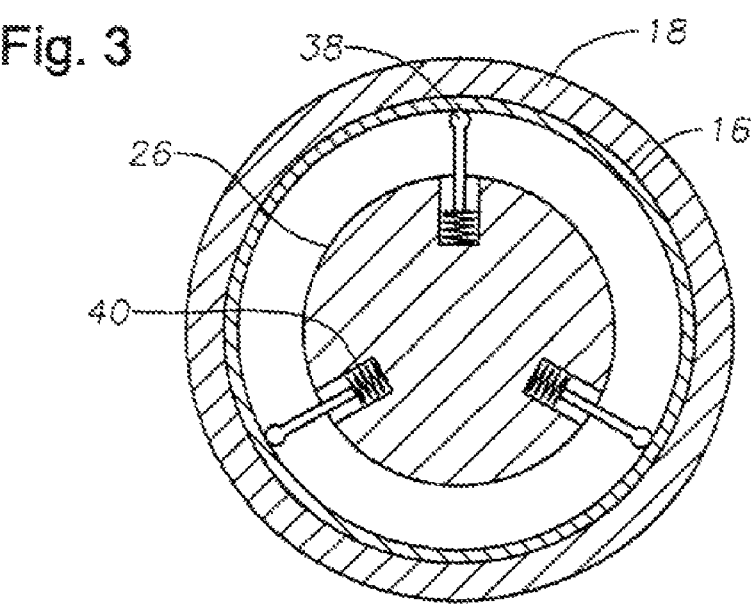

US 8,030,946 B2

IN-PIPE COATING INTEGRITY MONITOR FOR VERY LONG PIPES

RELATED APPLICATIONS

This patent application is a continuation-in-part of U.S. patent application Ser. No. 11/844,845, filed on Aug. 24, 2007, titled "IN-PIPE COATING INTEGRITY MONITOR FOR VERY LONG PIPES," now U.S. Pat. No. 7,768,270 which claims priority to and the benefit of US. patent application Ser. No. 60/839,884, filed on Aug. 24, 2006, titled "IN-PIPE COATING INTEGRITY MONITOR FOR VERY LONG PIPES," each incorporated herein by reference in its entirety.

BACKGROUND

1. Field of Invention

The present invention relates, in general, to the inspection of pipe coatings and, more specifically, to a tether-free piggable inspection device capable of reading and storing data relating to holiday detection and pipeline coating thickness in very long pipelines.

2. Description of Related Art

Internal non-conductive coating in pipelines provides protection, prevents corrosion, and improves the rate of liquid and gas transfer. In order for the pipe to be adequately protected, the layers of coating must be uniform, continuous and in compliance with the range of thickness values specified by the client. To verify these conditions, it is necessary to perform tests either between coating layers or after the final coat is applied. If a defect is found, a new coat will be applied and a new test must be run to certify the repair success.

Coating thickness measurement and holiday detection (holidays are also known as pinholes, voids, discontinuities, etc.) are two very common procedures that can provide an accurate diagnosis of the coating integrity. Among several methods, thickness measurement can be performed by using magnetic induction, Eddy currents or ultrasound waves; depending on the coating and pipe structures. Holiday detection is most commonly performed by positioning the coating between the positive and negative terminals of a high voltage power supply creating a high resistance path unless a coating discontinuity is present, in which case the circuit will close triggering an alarm.

Conventional testing devices utilize one of the two above mentioned procedures; they either measure coating discontinuities (i.e., the presence of a holiday) or coating thickness. Moreover, most of these tools are used for external measurement, and, in case the measurement is internal to the pipe, the tool's reach is limited to few feet. There is a need in the art for an inspection tool which monitors the internal coating integrity throughout the entire length of the pipeline which, in the case of a coiled tubing or flow line pipes, can be as long as several thousand feet.

It is an object of the present invention to provide a state of the art pipeline inspection tool that will perform coating thickness measurement and holiday detection for internal pipe inspections, tether free and battery operated.

SUMMARY OF INVENTION

In view of the foregoing, embodiments of the present invention provide systems, methods and program products to detect holidays and read and store coating thickness values in very long conductive pipes, along with distance values for further off-line analysis. The inspection tool, according to an embodiment of the present invention, includes a plurality of thickness probes, a data storage device, a control unit, one or more navigation wheels and a holiday detector that uses an electric conductive medium, such as gas or other fluid, as the ground connection. A closed loop configuration can be adopted to allow the system to autocorrect itself for different coating thicknesses along the pipe.

Various embodiments of the present invention provide systems, methods and program products related to a tether-free piggable pipe inspection device which includes a thickness sensor having one or more probes for measuring the thickness of the internal coating of the pipe, a holiday detector for detecting holidays within the internal coating along the length of pipe that is configured to trigger when holidays are present within the internal coating at a given location under evaluation. According to an embodiment of the present invention, the holiday detector is further configured to employ an adjustable voltage adjusted to maintain the voltage applied at the given location to between a value at or above a breakdown voltage of environmental fluid (e.g., air) in presence of a holiday at the given location (when so existing) and less than a breakdown voltage of the internal coating for a measured thickness at the given location in absence of a holiday (based on the properties of the coating) responsive to the measurements of the changes in the thickness of the internal coating along the length of pipe.

According to an embodiment of the present invention, the inspection device includes an electrode integral with or otherwise operably coupled to a holiday detector to apply the adjustable test voltage of the holiday detector to the surface of the internal coating. According to a preferred configuration, the one or more probes of the thickness sensor are positioned in front of the electrode associated with a holiday detector as the pipe inspection device moves through the pipe so that thickness data is received from the one or more probes for the given location along the internal coating to be measured prior to the voltage being applied to the given location along the internal coating. This configuration allows the holiday detector to utilize the thickness measurements for the given location as a reference by which to adjust the test voltage to be applied to the internal coating prior to the electrode reaching the given location so as to avoid damaging the coating.

According to such configuration, the holiday detector can increase the test voltage from that of its current setting when the thickness of the internal coating increases (is thicker than the prior measured thickness) to enhance detection accuracy, and can decrease the test voltage from that of its current setting when the thickness of the internal coating decreases (is thinner than the prior measured thickness) to prevent damage to the internal coating resulting from application of a voltage which exceeds the breakdown voltage of the internal coating at the given location.

According to various embodiments of the present invention, a sealing mechanism is placed behind the holiday detector to allow a conductive fluid to be injected into the pipe without coming into contact with the holiday detector. The conductive fluid is coupled to a grounding point. When the holiday detector reaches a holiday along the coating, the system voltage is conducted from the holiday detector to the pipe wall, then through the conductive fluid and back to holiday detector, thereby forming a closed circuit without the need of a tethered wire.

Embodiments of the present invention also include a method for inspecting an internal coating of a length of pipe. According to an example of an embodiment, such method can include the steps of measuring a thickness of an internal coating of a length of pipe to define thickness measurements, modifying a voltage applied to a surface of the coating at a given location along the coating to maintain the applied voltage between a value at or above a breakdown voltage of environmental fluid in presence of a holiday at the given location (when so existing) and a value less than the breakdown voltage of the coating for a measured thickness thereof at the given location responsive to the changes in the measured thickness of the coating, and detecting the presence of the holidays (when so existing). According to the exemplary configuration, the coating thickness measurements for the given location along the coating are made prior to the voltage being applied to the given location along the coating so that the voltage is modified in response to the measurements to prevent exceeding the breakdown voltage of the coating at the given location.

To enhance performance, the step of modifying a voltage applied to a surface of the coating at the given location along the coating includes or otherwise encompasses the steps of decreasing the adjustable test voltage in response to the thickness measurement to prevent exceeding a breakdown voltage of the coating at the given location when the thickness measurement indicates a decrease in thickness of the coating from that of a prior measurement at a corresponding prior tested adjacent location, and increasing the adjustable test voltage in response to the thickness measurement to enhance detection performance when the thickness measurement indicates an increase in thickness of the coating from that of a prior measurement at a corresponding prior tested adjacent location.

Embodiments of the present invention also include a tangible computer readable medium embodying a set of instructions, that when executed by an onboard or external control unit or other form of computer, cause the computer to perform various operations related to inspecting an internal coating along a length of pipe. The operations can include, for example, determining measurements of a thickness of an internal coating along a length of pipe using one or more probes, modifying a test voltage to be applied to the internal coating at a given location along the internal coating responsive to the thickness measurements indicating a change in the thickness of the internal coating along the length of pipe, and detecting the presence of holidays within the internal coating along the length of pipe when existing responsive to application of the voltage thereto.

According to this exemplary embodiment, the operation of modifying a voltage of the holiday detector can include the operation of modifying the voltage to maintain a value at or above a breakdown voltage of environmental fluid in the presence of a holiday at the given location (when so existing) and less than a breakdown voltage of the internal coating for a measured thickness at the given location in absence of a holiday responsive to the determined thickness measurements. In this exemplary embodiment, the measurements received from the one or more probes for the given location along the internal coating are performed at a time prior to the voltage being applied to the given location along the internal coating by an electrode associated with a holiday detector so that the voltage may be decreased when the thickness of the internal coating decreases to thereby prevent damage to the coating, and can be correspondingly increased when the thickness of the internal coating increases to thereby enhance detection performance.

BRIEF DESCRIPTION OF DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 1 is an axial cut view of the pipe and the holiday detector circuit architecture according to the prior art;

FIG. 3 is a front facing cross sectional view of the pipe and thickness sensor with three probes distributed 120 degrees apart according to an exemplary embodiment of the present invention;

DETAILED DESCRIPTION OF INVENTION

Figure 2:
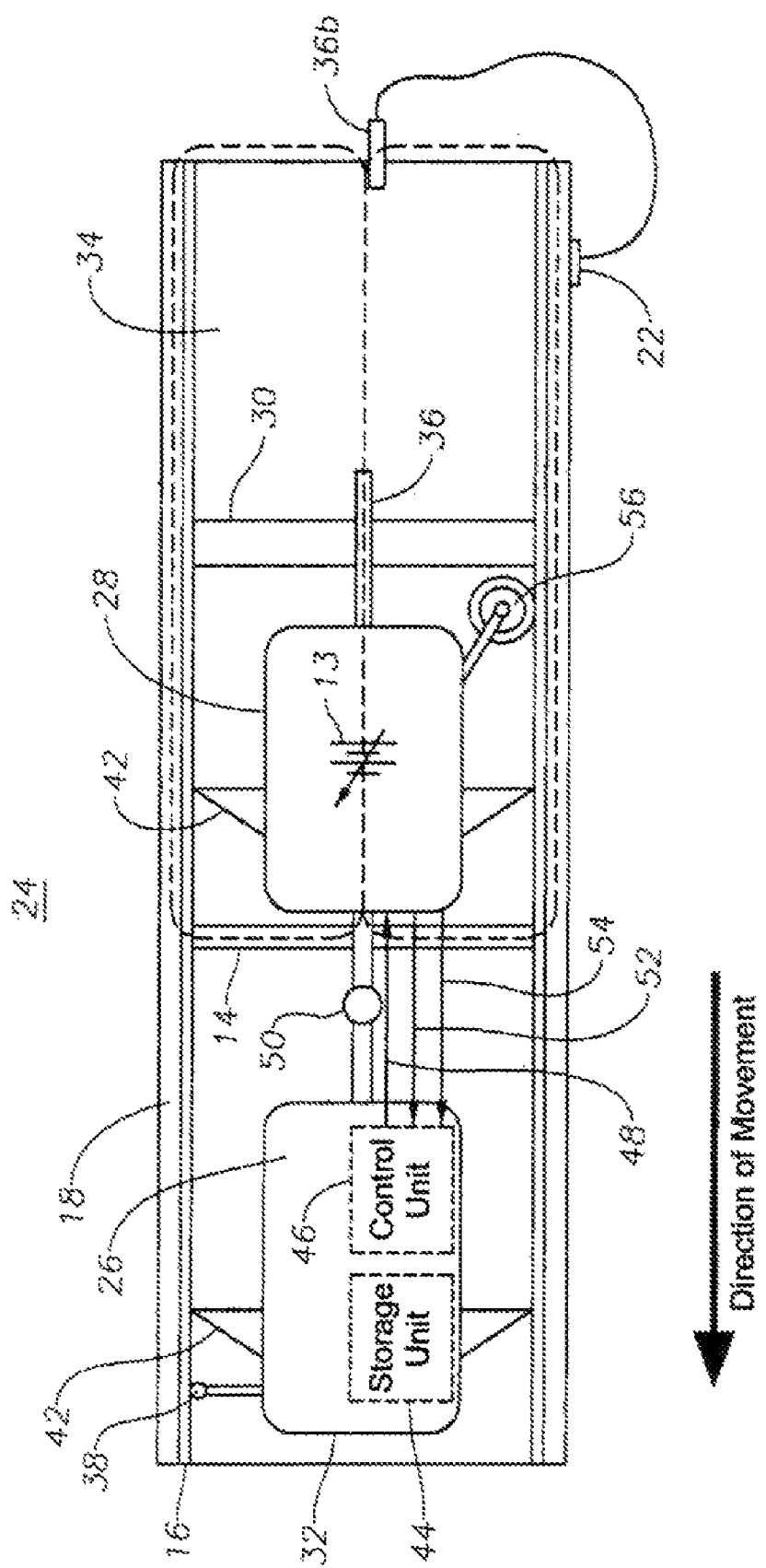
FIG. 2 is an axial cut view of the pipe along with a system according to an exemplary embodiment of the present invention.

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout.

FIG. 1 illustrates a traditional holiday detection apparatus which operates by detecting the current flow in circuit 10. Circuit 10 supplies a constant voltage source 12 of the holiday detector to test electrode 14 to the material under test, which in the case of FIG. 1 is a pipe coating 16, which is typically some form of non-conductive substrate. Coating 16 is applied to the pipe wall 18, which is typically a conductive substrate, such as steel or concrete. Concrete is conductive due to the electrically conductive matter contained within it. Pipe wall 18 is connected back to circuit 10 of the holiday detector by its earth lead 20. Circuit 10 is typically connected to a grounding point 22 on the exterior of pipe wall 18.

If there are no faults (i.e., holidays) in coating 16, then no current will flow from electrode 14 to pipe wall 18 due to the resistive nature of coating 16. When the electrode passes over a fault, the high voltage jumps the gap caused by the fault between coating 16 and the electrode. When this occurs, current flows and the Holiday Detector detects this and activates its alarm. The test voltage level used depends on the type of fault you are trying to find and the electrical properties of the coating material 16.

There are problems associated with traditional Holiday detection systems. One problem arises when it is not possible to connect the earth lead to the pipe wall 18, thereby preventing circuit 10 from closing even in the presence of a Holiday. This will typically occur in a pipe that is extremely long and does not maintain a straight-line geometry. Such is the case of coiled tubing and flow line pipes, with lengths of up to 30,000 feet and coils in reels with a Radius of Curvature down to 75 inches. If the Holiday Detector is allowed to travel from beginning to end of the pipe and it is intended to use an earth lead, this lead should be at least as long as the pipe. However, there are many disadvantages to this tethered earth lead approach because it adds prohibitive values of resistance, friction and increases the complexity to the system.

FIG. 2 illustrates an exemplary embodiment of the present invention which addresses these deficiencies in traditional systems. Pipe inspection system 24 includes thickness sensor 26, holiday detector 28 and seal 30. System 24 is a tether-free piggable device which utilizes a motorized device to move through the interior of pipe 32. However, in the alternative, system 24 may be forced through pipe 32 by conductive fluid 34, which is pressurized and pumped into pipe 32 behind seal 30. In this instance, seal 30 would serve to seal system 24 against any damage from the conductive fluid.

Further referring to the exemplary embodiment of FIG. 2, as system 24 moves along the interior of pipe 32, it is led by thickness sensor 26. A plurality of sensor probes 38 are spaced around the exterior housing of thickness sensor 26 in order to detect the thickness of coating 16. Probes 38 can take any form known in the art, such as, for example, those sensors utilizing principles of induction. These thickness probes have a hardened contact surface to avoid material wearing. An exemplary embodiment of thickness sensor 26 is illustrated in FIG. 3, which shows a front facing view of the system as it moves through pipe 32 wherein three probes 38 are circumferentially spaced around the exterior of thickness sensor 26 at 120° angles. Please note, however, that any number of probes may be utilized dependant upon the desired amount of spatial granularity of the design.

Further referring to the exemplary embodiment of FIG. 3, a spring mechanism 40 is attached to the base of each probe 38 for radial adjustment to ensure firm contact with coating 16. As system 24 moves along the interior of pipe 32, the thickness of coating 16 varies. Therefore, in order for probes 38 to remain in constant firm contact with coating 16, springs 40 must allow for radial adjustment. If not, crucial thickness measurements will be missed by system 24, possibly resulting in damage to coating 16 or missed holiday readings. Although not shown, sensor probes 38 also includes a lift spring mechanism which enables probes 38 to remain perpendicular to the surface of coating 16. In addition, a plurality of support members 42 (FIG. 2) are spaced around the exterior of thickness sensor 26 in order to ensure that sensor 26 remains centered within pipe 32.

Thickness sensor 26 includes a storage unit 44 and control unit 46. After probes 38 read the thickness measurements corresponding to coating 16, a CPU (not shown) instructs a processor (not shown) to transmit the measurements to control unit 46. Such readings can be in the form of digital or analog data and stored in storage unit 44 and later downloaded for further analysis such as, for example, making sure the thickness of coating 16 is within an acceptable range. Control unit 46 is in charge of providing a feed back signal 48 to holiday detector 28 instructing detector 28 to increase or decrease the adjustable voltage 13 being supplied to coating 16 based upon the thickness measurements received from probes 38. Control unit 46 constantly monitors the thickness of coating 16 via probes 38. Such readings, for example, can be on the order of thousands per second. Although not shown, system 24 also includes an on-system battery and transformer circuitry to step up or step down the voltage 13 as instructed by control unit 46.

For a uniform coating, a constant test voltage value can be used. However, if the coating is not uniform throughout the whole pipe length, a constant test voltage value could introduce inevitable failures. Accordingly, the voltage level to be applied by adjustable voltage source 13 is limited by two values: the environmental fluid (e.g., air) breakdown voltage and the coating breakdown voltage. That is, the voltage should be high enough to break through the environmental fluid in the presence of a holiday, but low enough not to break through the coating in the absence of a holiday. To avoid system failure in the event of an uneven coating along the pipeline, control unit 46 provides a feed back signal 48 to holiday detector 28, thereby changing the system from an open to a closed control loop. As discussed, the main objective of feedback signal 48 is to vary the test voltage value accordingly with the coating thickness. As the thickness of coating 16 diminishes, the test voltage value being supplied by adjustable voltage source 13 can be decreased, and, as the thickness of coating 16 increases, the test voltage value being supplied by adjustable voltage source 13 can be increased.

Further referring to the exemplary embodiment of FIG. 2, holiday detector 28 is located behind thickness sensor 26 in the forward facing direction. A universal joint 50, or other suitable connector, is used to connect holiday detector 28 to thickness sensor 26, thereby allowing system 24 to navigate through curved pipes. A number of electrical connectors extend between holiday detector 28 and thickness sensor 26 in order to allow for bi-directional communication of control and data signals between the two. However, in the alternative, other methods of communication may be utilized, such as, for example, wireless communication links. As illustrated in FIG. 2, these electrical connectors include holiday detection signal link 52 and distance signal link 54, as well as feedback signal link 48 discussed previously. Any variety of data can be transmitted as desired.

Holiday detector 28 is used to detect the presence of holidays within coating 16. Holiday detector 28 includes support members 42 which ensure it remains centered as discussed in relation to thickness sensor 26. Holiday detector 28 also includes an adjustable voltage source 13 which supplies a test voltage to electrode 14 located at the front of holiday detector 28. Electrode 14 can take various forms such as, for example, a conductive brush with full circumferential contact with coating 16. In any event, electrode 14 will remain in constant contact with the surface of coating 16. After control unit 46 receives the thickness measurements read from coating 16 via probes 38, control unit 46 processes the measurements and outputs feedback signal 48 which instructs holiday detector 28 to apply a voltage level corresponding to the thickness measurements. As such, holiday detector 28 can increase the voltage appropriately when the thickness of coating 16 increases and decrease the voltage appropriately when the thickness decreases.

Holiday detector 28 also includes navigation wheel 56 to measure distance along the length of pipeline 32. Although wheel 56 is shown attached to holiday detector 28, it may be located elsewhere in the system. Also, system 24 may include a plurality of wheels 56 for redundancy purposes. In this exemplary embodiment, control unit 46 will also be monitoring holiday detector 28, and instead of triggering an alarm every time a holiday is detected, control unit 46 will save the value of distance where the detection occurred in storage unit 44, therefore keeping track of every holiday detected along coating 16 of pipe 32. This data is transmitted back to control unit 46 or storage unit 44 via the holiday detection signal link 52 and distance signal link 54. In addition, the system 24 may also store the thickness measurements and their corresponding locations based upon readings from navigation wheel 56.

Further referring to the exemplary embodiment of FIG. 2, seal 30 is located at the rear of holiday detector 28 in order to prevent conductive fluid 34 from damaging the system electronics and to prevent false alarms of holidays (i.e., short circuits). As discussed previously, system 24 can be either self-propelled or subjected to pressure from conductive fluid 34 in order to move it through pipe 32. In either case, however, some form of conductive fluid will be present behind system 24. As such, seal 30 will ensure that no fluid reaches test electrode 14, otherwise a short circuit will occur. A ground electrode 36 is coupled to the circuitry of holiday detector 28 and extends through seal 30 to contact conductive fluid 34. Seal 30 will allow conductive fluid 34 to make contact with ground electrode 36 while preventing contact between the conductive fluid 34 and test electrode 14. A secondary ground electrode 36b is located at the entry point of conductive fluid 34 and is coupled to grounding point 22.

As discussed above, in order for system 24 to travel inside the pipe, a conductive fluid 34 could be pressurized and pumped to pig it through, or, system 24 could also have its own motor unit which will provide self-propulsion to reduce or eliminate the pressure needed behind it. In addition, the present invention utilizes the conductive properties of certain fluids, such as tap water, to act as a ground connection for system 24. As such, the present invention does not require a tether to be extended throughout the length of pipe 32 as employed in traditional inspection systems. Although water is described as the conductive fluid within this disclosure, any other fluid suitable for pigging and electrical conductivity can be used.

Since there is no tethered ground "wire" employed in the present invention, the conductive fluid 34 is used as the ground connection closing the circuit. An example of conductive fluid 34 is water, which has a very high dielectric strength but is also a very good conductor (i.e., it has low resistivity) when it contains impurities. At this point, it would be useful to define Resistivity:

Resistivity ($\rho$) is a constant and is defined as:

$$\rho = (R*A)/L, \text{ (Ohms Foot)}$$

where R is the resistance value, A is the cross section area in square foot and L is the Pipe (or conductor) length in Feet. Therefore, the units for the resistivity $\rho$ are (Ohms×Foot) (or any other unit of length). Its reciprocal, conductivity $\kappa$, has units of (Siemens/foot). Then, by knowing the resistivity of the conductive fluid, it is possible to determine the total resistance "R" of a certain pipe section filled with the conductive fluid given the values of "A" and "L".

Figure 4:
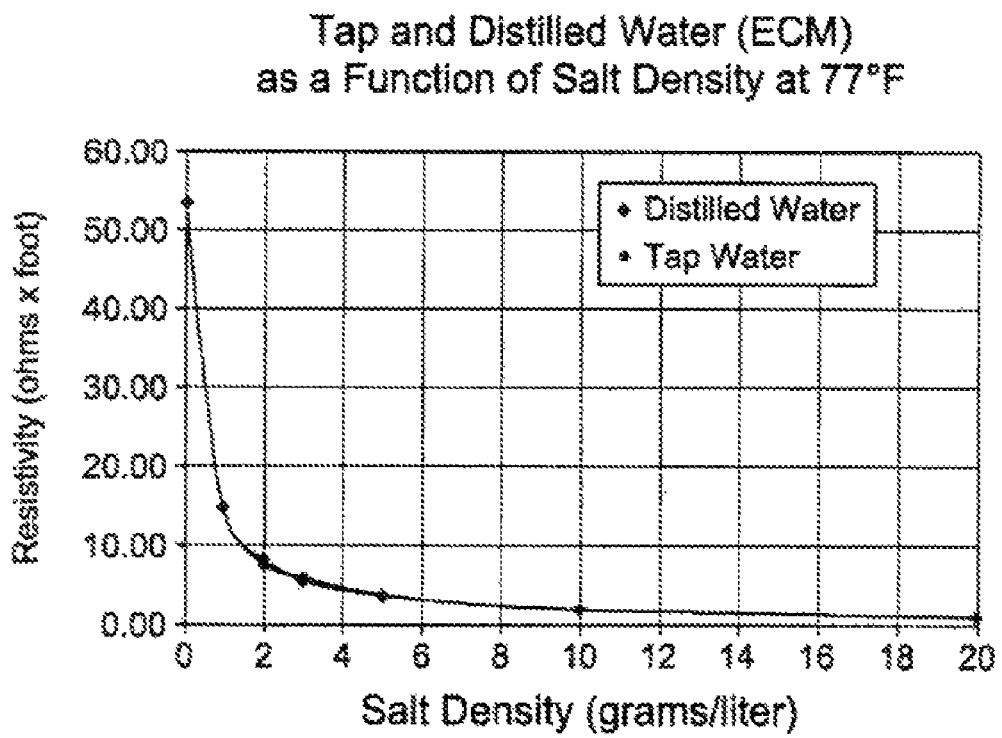
FIG. 4 illustrates a graph representing an example of water used as a conductive fluid at a constant temperature of 77° F., where the resistivity of distilled and tap water are shown as a function of salt density. Resistivity is expressed in Ohms× Foot and salt density in grams/liter.

Referring to the FIG. 4, a graph is illustrated showing resistivity of Distilled and Tap water as a function of salt density at a constant temperature of 77° F. Resistivity is expressed in (Ohms×Foot) and salt density in (grams/liter). After performing several experiments in which impurities were added to Distilled and Tap water, which could both be used as conductive fluid 34, the results showed that the Resistivity values obtained are suitable for using Distilled and Tap Water as a ground connection provided that the desired test voltage values are in the order of hundreds of volts and test current values are in the order of micro Amps. These results conclude that conductive fluid Resistivity can be easily controlled by adding impurities and that these fluids can be used as a ground connection.

Figure 5:
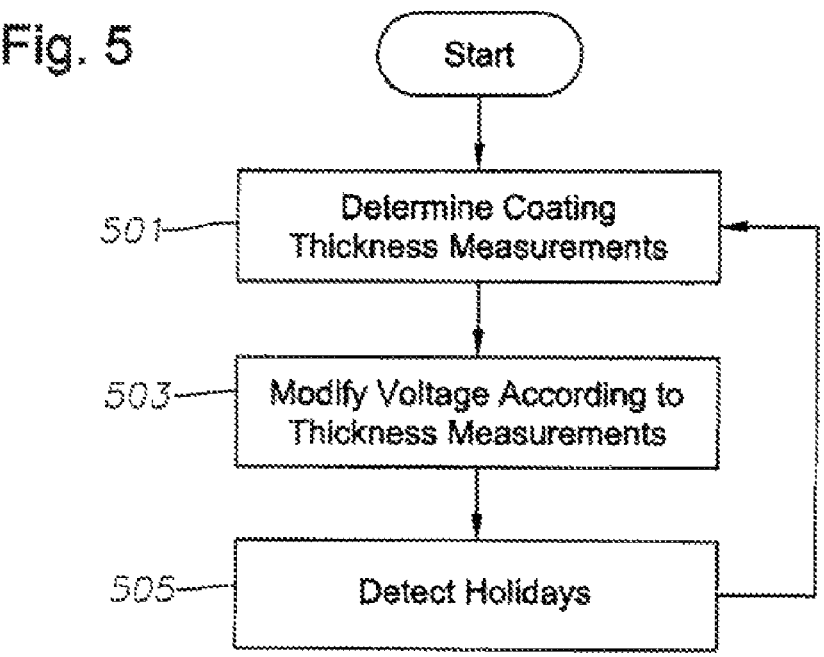
FIG. 5 is a flow chart illustrating a method according to an exemplary embodiment of the present invention.

Referring to FIG. 5, an exemplary method employing an embodiment of the present invention will now be described. At step (501), using probes 38, the processor of control unit 46 determines the thickness measurements of coating 16 as it moves through pipe 32. At step (503), the control unit 46 will transmit feedback signal 48 to holiday detector which is responsive to the changes in the thickness measurements received from probes 38. Since thickness sensor 26 is located in front of holiday detector 28, the measurements received from probes 38 for a given location along the coating 16 are measured at a time prior to the voltage being applied to that same location along coating 16. As such, the voltage applied to coating 16 via electrode 14 will be modified such that holiday detector 28 will increase voltage 13 when the thickness of coating 16 increases and decrease voltage 13 when the thickness decreases, thereby only triggering when holidays are present within coating 16 without causing damage to coating 16.

Should electrode 14 contact a holiday as system 24 moves through pipe 32, the voltage applied through electrode 14 will "jump" across the holiday to pipe wall 18, where it will proceed to grounding electrode 36b. Once the current reaches grounding electrode 36b, conductive fluid 34 acts as an electrical conductor creating a closed circuit allowing the current to flow back to the circuitry of holiday detector 28, thereby indicating a current spike corresponding to the presence of the holidays at step (505). System 24 may also store a number of values in storage unit 44 such as, for example, the locations of the holidays and/or the thicknesses of coating 16 and their corresponding locations for further analysis and/or repair of the pipeline.

The illustrated embodiment of the present invention utilizes the circuit architecture discussed previously whereby conductive fluid 34 is used instead of an earth lead to close the circuit. As long as coating 16 is uniform and maintains a constant thickness value, this system will work with a constant test voltage value. However, if the thickness changes along pipe 32, the test voltage is changed accordingly. Coating thickness probes 38 in front of the holiday detector 28 will provide a feedback signal 48 to system control unit 46. Control unit 46 will then adjust the test voltage to assure that the circuit will trigger only in the presence of a holiday. The completed hybrid system of the illustrated embodiment of the present invention consists then of two or more cooperative units, namely thickness sensor 26 and Holiday detector 28, a Control Unit 46, a high voltage power supply 13 and batteries. By implementing this hybrid-closed loop architecture, the system is able not only to detect holidays accurately but also to store values of coating thickness and distance, allowing further off-line data analysis.

It is important to note that while embodiments of the present invention have been described in the context of a fully functional system and method embodying the invention, those skilled in the art will appreciate that the mechanism of the present invention and/or aspects thereof are capable of being distributed in the form of a computer readable medium storing a set of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links capable of storing the set of instructions. Such tangible media (i.e., not transitory propagating signal) can include, for example, both operating instructions and/or instructions related to the system and the method steps described above.

It is to be understood that the invention is not limited to the exact details of construction, operation, exact materials, or embodiments shown and described, as modifications and equivalents will be apparent to one skilled in the art. For example, various components, such as the control and storage units may be stand-alone units located elsewhere within system 24 or may even be remotely located. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

The invention claimed is:

1. A system for inspecting an internal, non conductive coating along a length of pipe, the system including a pipe inspection device, the pipe inspection device comprising:
   a thickness sensor for determining measurements of a thickness of the internal coating along the length of pipe defining thickness measurements, the thickness sensor comprising one or more probes each having a support mechanism which provides substantially constant contact with a surface of the internal coating so that values of the thickness measurements are responsive to changes in the thickness of the internal coating; and
   a holiday detector for detecting holidays within the internal coating along the length of pipe, the holiday detector configured to trigger when holidays are present within the internal coating at a given location under evaluation along the internal coating and further configured to employ an adjustable voltage adjusted to maintain the voltage applied at the given location to between a value at or above a breakdown voltage of environmental fluid in presence of a holiday at the given location when so existing and less than a breakdown voltage of the internal coating for a measured thickness at the given location in absence of a holiday responsive to the measurements of the changes in the thickness of the internal coating along the length of pipe.

2. A system as defined in claim 1, wherein the adjustable voltage is an adjustable test voltage, and wherein the pipe inspection device further comprises:
   an electrode positioned to apply the adjustable test voltage of the holiday detector to the surface of the internal coating; and
   wherein the thickness sensor is located in front of the electrode as the pipe inspection device moves through the pipe so that thickness data is received from the one or more probes for the given location along the internal coating to be measured prior to the voltage being applied to the given location along the internal coating so that the voltage may be increased by the holiday detector when the thickness of the internal coating increases to enhance accuracy of holiday detection and decreased when the thickness of the internal coating decreases to prevent damage thereto.

3. A system as defined in claim 2,
   wherein the pipe inspection device comprises a tether-free piggable pipe inspection device; and
   wherein the holiday detector comprises an adjustable voltage source that supplies the adjustable voltage to an electrode, the holiday detector configured to adjust the voltage responsive to changes in thickness of the internal coating along the length of pipe.

4. A system as defined in claim 2,
   wherein the thickness sensor and the holiday detector each have separate and spaced apart exterior housings; and
   wherein the pipe inspection device further comprises a connector positioned to connect the thickness sensor to the holiday detector.

5. A system as defined in claim 4, wherein the connector comprises:
   a universal joint positioned to facilitate navigation of the separate and spaced apart thickness sensor and holiday detector through the curved pipes.

6. A system as defined in claim 4, wherein the pipe inspection device further comprises:
   a first plurality of support members connected to the housing of the thickness sensor to ensure that the thickness sensor remains substantially centered within the pipe; and
   a second plurality of support members connected to the housing of the holiday detector, the second plurality of support members positioned to support the holiday detector independent of support provided to the thickness sensor by the first plurality of support members.

7. A system as defined in claim 1, wherein the one or more probes comprises at least three probes spaced around the exterior housing of the thickness sensor, each of the at least three probes having a hardened pipe-contact surface to thereby reduce material wearing, and a spring mechanism attached to a base of each probe for radial adjustment to ensure a firm continuous contact with the internal coating along the length of pipe.

8. A system as defined in claim 1,
   wherein the adjustable voltage is an adjustable test voltage;
   wherein the pipe inspection device includes an electrode operably coupled to the holiday detector and positioned to apply the adjustable test voltage of the holiday detector to the surface of the internal coating; and
   wherein the thickness sensor is located in front of the holiday detector so that as the pipe inspection device moves through the pipe, thickness measurements for the given location along the internal coating to be measured are made prior to the voltage being applied to the given location along the internal coating so that the voltage may be increased when the thickness of the internal coating increases and decreased when the thickness of the internal coating decreases to prevent damage thereto.

9. A system as defined in claim 1,
   wherein the pipe inspection device comprises a tether-free piggable pipe inspection device; and
   wherein the thickness sensor of the tether-free piggable pipe inspection device further comprises:
      a mechanism which determines values corresponding to thickness values of the internal coating along the length of pipe and one or more of the following: locations of the holidays along the length of pipe, and locations of the thickness values; and
      a storage unit for storing the values for further analysis of the length of pipe.

10. A non-transitory computer readable medium that is readable by a computer, the computer readable medium comprising a set of instructions that, when executed by a computer, causes the computer to perform the following operations:
   determining measurements of, a thickness of an internal coating along a length of pipe using one or more probes;
   modifying a voltage, of a holiday detector to be applied to the internal coating at a given location along the internal coating responsive to the measurements of the changes in the thickness of the internal coating along the length of pipe, the operation of modifying a voltage of the holiday detector including modifying the voltage to maintain a value at or above a breakdown voltage of environmental fluid in presence of a holiday at the given location when so existing and less than a breakdown voltage of the internal coating for a measured thickness at the given location in absence of a holiday responsive to the determined thickness measurements; and detecting the presence of holidays within the internal coating along the length of pipe when existing responsive to application of the voltage thereto.

11. A non-transitory computer readable medium as defined in claim 10, wherein the measurements received from the one or more probes for the given location along the internal coating are performed at a time prior to the voltage being applied to the given location along the internal coating so that the voltage may be increased when the thickness of the internal coating increases and decreased when the thickness of the internal coating decreases to prevent damage thereto.

12. A non-transitory computer readable medium as defined in claim 10, the computer readable medium having a set of instructions that, when executed by a computer, causes the computer to perform the operation of recording values corresponding to one or more of the following:

locations of the holidays along the length of pipe;

thickness values of the internal coating along the length of pipe; and locations of the thickness values for further analysis of the length of pipe.

13. A non-transitory computer readable medium as defined in claim 10, wherein the voltage to be applied to the surface of the coating defines an adjustable test voltage, and wherein the operation of modifying a voltage to be applied to a surface of the coating at the given location along the coating includes the operations of:

measuring a decrease in thickness of the coating from a prior measurement at a corresponding prior tested adjacent location; and decreasing the adjustable test voltage in response to the thickness measurement to prevent exceeding a breakdown voltage of the coating at the given location.

14. A non-transitory computer readable medium as defined in claim 10, wherein the voltage to be applied to the surface of the coating defines an adjustable test voltage, and wherein the operation of modifying a voltage to be applied to a surface of the coating at the given location along the coating includes the operations of:

measuring an increase in thickness of the coating from a prior measurement at a corresponding prior tested adjacent location; and increasing the adjustable test voltage in response to the thickness measurement.

15. A method for inspecting an internal coating of a length of pipe, the method comprising the steps of:

measuring a thickness of an internal coating of a length of pipe to define thickness measurements, values of the thickness measurements reflecting changes in the thickness of the coating;

modifying a voltage applied to a surface of the coating at a given location along the coating to maintain the applied voltage between a value at or above a breakdown voltage of environmental fluid in presence of a holiday at the given location when so existing and a value less than a breakdown voltage of the coating for a measured thickness thereof at the given location in absence of a holiday responsive to the changes in the measured thickness of the coating; and detecting the presence of the holidays.

16. A method as defined in claim 15, wherein the coating thickness measurements for the given location along the coating are made prior to the voltage being applied to the given location along the coating so that the voltage is modified in response to the measurements to prevent exceeding the breakdown voltage of the coating at the given location.

17. A method as defined in claim 15, wherein the voltage applied to the surface of the coating defines an adjustable test voltage, and wherein the step of modifying a voltage applied to a surface of the coating at the given location along the coating includes the steps of:

measuring a decrease in thickness of the coating from that of a prior measurement at a corresponding prior tested adjacent location; and decreasing the adjustable test voltage in response to the thickness measurement to prevent exceeding a breakdown voltage of the coating at the given location.

18. A method as defined in claim 15, wherein the voltage applied to the surface of the coating defines an adjustable test voltage, and wherein the step of modifying a voltage applied to a surface of the coating at the given location along the coating includes the steps of:

measuring an increase in thickness of the coating from that of a prior measurement at a corresponding prior tested adjacent location; and increasing the adjustable test voltage in response to the thickness measurement.

19. A method as defined in claim 15, wherein the step of measuring a thickness of an internal coating includes using one or more probes, the probes having a support mechanism which allows for constant contact with a surface of the internal coating so that the measurements are responsive to changes in the thickness of the internal coating.

20. A method as defined in claim 15, further comprising the steps of:

activating a trigger when holidays are present within the coating; and recording values corresponding to one or more of the following:

locations of the holidays along the length of pipe, thickness values of the coating along the length of pipe, and locations of the thickness values used for further analysis of the length of pipe.

* * * * *